(12) United States Patent
Werneth et al.

(10) Patent No.: US 8,682,410 B2
(45) Date of Patent: Mar. 25, 2014

(54) MULTI-ARRAY MONOPHASIC ACTION POTENTIAL MEDICAL DEVICE

(75) Inventors: Randell L. Werneth, San Diego, CA (US); Meleze Hocini, Pessac (FR); Mark T. Stewart, Lino Lakes, MN (US); Dan Wittenberger, L'ile Bizard (CA); Timothy J. Corvi, Carlsbad, CA (US); Michael Lau, Fremont, CA (US); Vinod Sharma, Maple Grove, MN (US)

(73) Assignee: Medtronic Ablation Frontiers LLC, NE Minneapolis, MN (US)

( * ) Notice: Subject to any disclaimer, the term of this patent is extended or adjusted under 35 U.S.C. 154(b) by 286 days.

(21) Appl. No.: 13/044,698

(22) Filed: Mar. 10, 2011

(65) Prior Publication Data

US 2012/0232374 A1    Sep. 13, 2012

(51) Int. Cl.
*A61B 5/042* (2006.01)
*A61B 18/14* (2006.01)

(52) U.S. Cl.
USPC ............................................ 600/374; 606/41

(58) Field of Classification Search
USPC ........................................................ 600/374
See application file for complete search history.

(56) References Cited

U.S. PATENT DOCUMENTS

| | | | |
|---|---|---|---|
| 4,682,603 A | | 7/1987 | Franz |
| 5,637,090 A | * | 6/1997 | McGee et al. ............... 600/374 |
| 5,711,298 A | * | 1/1998 | Littmann et al. ............ 600/374 |
| 5,836,875 A | * | 11/1998 | Webster, Jr. ................. 600/374 |
| 6,152,882 A | | 11/2000 | Prutchi |
| 6,405,067 B1 | | 6/2002 | Mest et al. |
| 6,615,483 B2 | * | 9/2003 | Lindegren ...................... 29/825 |
| 7,089,045 B2 | | 8/2006 | Fuimaono et al. |
| 2004/0092806 A1 | * | 5/2004 | Sagon et al. ................. 600/374 |
| 2008/0243214 A1 | * | 10/2008 | Koblish ........................ 607/115 |
| 2011/0028820 A1 | | 2/2011 | Lau et al. |

FOREIGN PATENT DOCUMENTS

| | | |
|---|---|---|
| EP | 0757575 B1 | 2/1997 |
| EP | 1125549 A2 | 8/2001 |
| EP | 1166714 A1 | 1/2002 |
| WO | 0042914 A1 | 7/2000 |

OTHER PUBLICATIONS

Franz, Michael R., Current Status of Monophasic Action Potential Recording; theories, measurements and interpretations, Cardiovascular Research, 41 (1999) 25-40.

* cited by examiner

*Primary Examiner* — Lee S Cohen
(74) *Attorney, Agent, or Firm* — Christopher & Weisberg, P.A.

(57) ABSTRACT

A medical device including a catheter having a shaft with a distal portion; a first plurality of substantially hemispherical electrodes coupled to the distal portion; a second plurality of substantially hemispherical electrodes coupled to the shaft proximal of the first plurality, where the second plurality of electrodes are oriented substantially orthogonal to the first plurality of electrodes; and an additional electrode coupled to the shaft. A console may have a processor in electrical communication with the first and second plurality of electrodes and the reference electrode, the processor programmed to obtaining a monophasic action potential recording from at least one of the first and second plurality of electrodes.

6 Claims, 10 Drawing Sheets

MULTI-ARRAY MONOPHASIC ACTION POTENTIAL MEDICAL DEVICE

CROSS-REFERENCE TO RELATED APPLICATION

N/A

STATEMENT REGARDING FEDERALLY SPONSORED RESEARCH OR DEVELOPMENT

N/A

FIELD OF THE INVENTION

The present invention relates to medical systems and methods for cardiac tissue diagnosis and treatment.

BACKGROUND OF THE INVENTION

Medical procedures are available for treatment of a variety of cardiovascular maladies, such as cardiac arrhythmias, atrial fibrillation, and other irregularities in the transmission of electrical impulses through the heart. As an alternative to open-heart surgery, many medical procedures are performed using minimally invasive surgical techniques, where one or more slender implements are inserted through one or more small incisions into a patient's body. Such procedures may involve the use of catheters or probes having multiple sensors, electrodes, or other measurement and treatment components to treat the diseased area of the heart, vasculature, or other tissue. Minimally-invasive devices are desirable for various medical and surgical applications because they allow for shorter patient recovery times compared to surgery, and for precise treatment of localized discrete tissues that are otherwise difficult to access. For example, catheters may be easily inserted and navigated through the blood vessels and arteries, allowing non-invasive access to areas of the body with relatively little trauma, while other minimally-invasive probes or instruments may be inserted into small openings and directed through targeted anatomy without significant impact or disruption to surrounding tissue.

One such example of a minimally invasive therapy involves the treatment of cardiac arrhythmias or irregular heartbeats in which physicians employ specialized cardiac assessment and treatment devices, such as a mapping and/or ablation catheter, to gain access to interior regions of a patient's body. Such devices may include tip electrodes or other ablating elements to create lesions or other anatomical effects that disrupt or block electrical pathways through the targeted tissue. In the treatment of cardiac arrhythmias, a specific area of cardiac tissue having aberrant electrical activity (e.g. focal trigger, slow conduction, excessively rapid repolarization, fractionated electrogram, etc.) is typically identified first before subsequent treatment. This localization or identification can include obtaining monophasic action potential ("MAP") electrograms of a particular cardiac region. Monophasic action potentials reproduce complete action potential of cardiac tissues including the repolarization time course of myocardial cells with high accuracy and provide precise information on local activation. MAP signals may be obtained by temporarily depolarizing selected tissue, with responsive electrical activity being recorded or otherwise monitored for an indication of aberrant electrical activity. After mapping and diagnosing aberrant tissue, a physician may decide to treat the patient by ablating the tissue.

Recording MAP signals and subsequently treating affected areas involve maneuvering selected diagnostic and treatment devices through restricted and sometimes tortuous pathways to access the desired tissue region. The restrictive environment surrounding the targeted tissue can reduce the ability of a device to be properly positioned to obtain the desired information and/or deliver the treatment needed. To provide more effective and efficient medical treatments, it is thus desirable to optimize the apparatus and method of use for the specific tissue to be treated, taking into account the characteristics of the tissue to be diagnosed and treated, as well as the location and pathway of access to the selected tissue.

SUMMARY OF THE INVENTION

The present invention advantageously provides a medical device, system, and method for treating a patient by obtaining monophasic action potential ("MAP") electrograms of cardiac tissue, either epicardially or endocardially, for the identification and treatment of electrical tissue disorders. In particular, a medical device includes a shaft having a distal portion, a first monophasic action potential electrode array coupled to the distal portion, a second monophasic action potential electrode array coupled to a lateral surface of the shaft proximal to the first array, and an additional electrode coupled to the shaft.

The second electrode array may be oriented substantially orthogonal to the first electrode array, and may include a plurality of electrodes positioned along a length of the shaft, the electrodes arranged in two rows approximately 180 degrees apart from one another. The shaft may be controllably deflectable within a defined plane, and the two rows of electrodes may be aligned in the plane. The first and second electrode arrays may include respective pluralities of substantially hemispherical shaped electrodes, which may be made of substantially non-polarizable material. The first electrode array may include a plurality of electrodes, four for example, that are equally spaced from a longitudinal axis defined by the shaft. The additional electrode may define a substantially cylindrical band circumscribing the shaft proximally of the second electrode array, a substantially semi-cylindrical band circumscribing approximately half of a circumference of the shaft, or a dome at the distal portion of the shaft, with the first electrode array circularly arranged around the dome. The additional electrode may be recessed at the distal portion of the shaft, substantially centered with respect to the first electrode array, and the device may also include a pacing electrode or electrode pair coupled to the shaft. The second electrode array may define at least one port in fluid communication with a supply of electrically conductive fluid. The medical device may also include a sheath covering a portion of the second electrode array; the sheath having a side aperture exposing another portion of the second electrode array. The second electrode array may also be a retractable needle.

A medical device is also provided, including a catheter having a shaft with a distal portion; a first plurality of substantially hemispherical electrodes coupled to the distal portion; a second plurality of substantially hemispherical electrodes coupled to the shaft proximal of the first plurality, where the second plurality of electrodes are oriented substantially orthogonal to the first plurality of electrodes; and an additional electrode coupled to the shaft. The device may also include a console having a processor in electrical communication with the first and second plurality of electrodes and the additional electrode, the processor programmed to obtaining a monophasic action potential recording from at least one of the first and second plurality of electrodes. The additional electrode may be recessed at the distal portion of the shaft.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Figure 1:
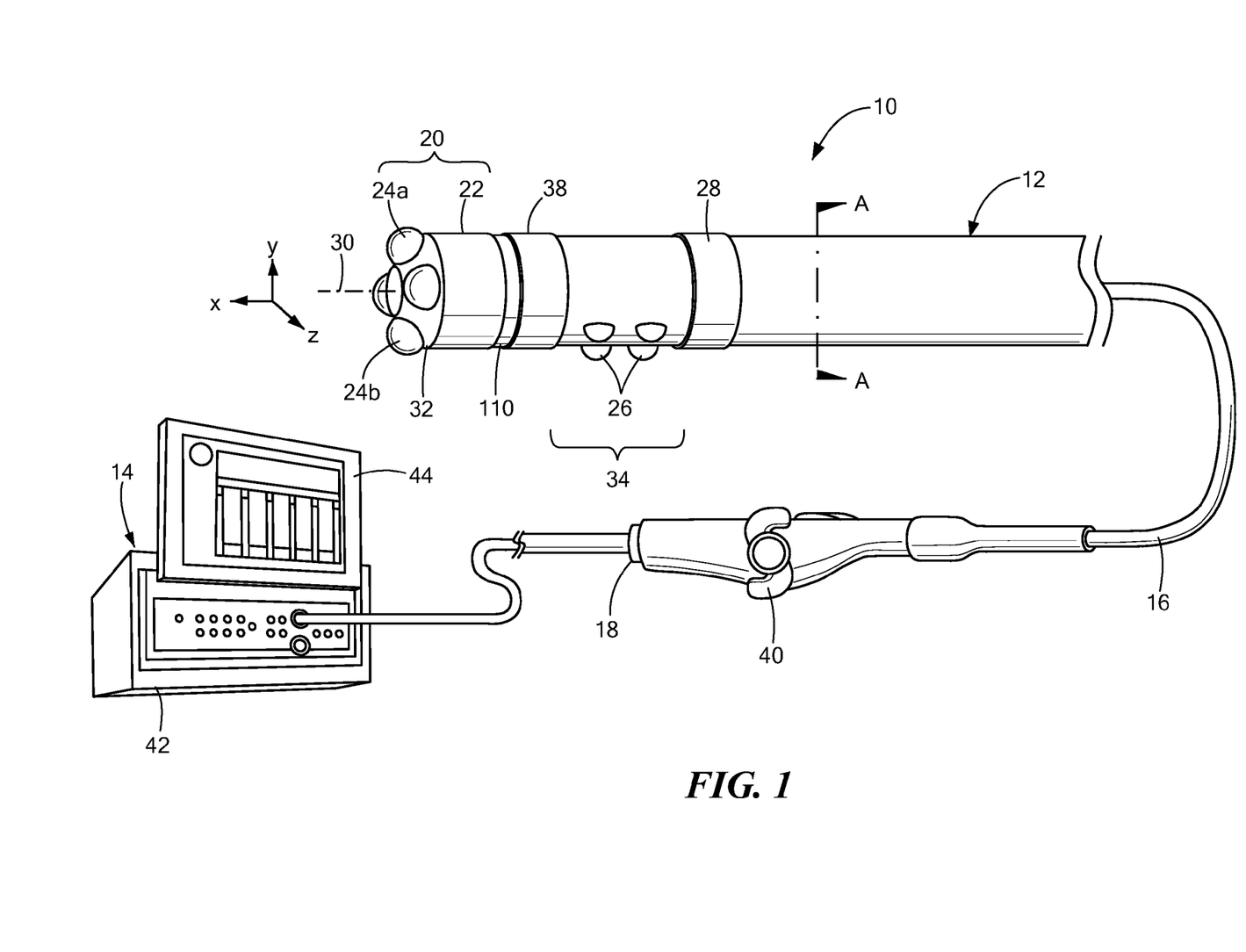
FIG. 1 is an illustration of an exemplary medical system constructed in accordance with the principles of the present invention.

The present invention provides medical devices, systems and methods for obtaining monophasic action potential electrograms for both endocardial and epicardial medical treatments. Referring now to the drawings in which like reference designators refer to like elements, there is shown in FIG. 1 an exemplary embodiment of a monophasic action potential ("MAP") electrogram device system constructed in accordance with the principles of the present invention, designated generally as 10. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein may be included in a variety of different combinations or configurations without departing from the scope and spirit of the invention.

As shown in FIG. 1, the medical system 10 generally includes a medical device 12 coupled to a console 14 or other operating equipment. The medical device 12 may be a catheter or surgical probe having diagnostic and/or treatment components positionable at or near a target tissue region. For example, the medical device 12 illustrated in FIG. 1 may include an elongate body or shaft 16 with proximal and distal portions. The shaft 16 may be both flexible and resilient, with sufficient column strength facilitating steady contact with tissue to improve signal fidelity in diagnosing contacted tissue as well as improve therapeutic thermal exchange between the device 12 and contacted tissue. The medical device 12 may further include a handle 18 affixed to the proximal portion of the shaft 16.

The device 12 may further include a first treatment assembly 20 coupled to the distal portion of the shaft 16, as well as a second treatment assembly 34 coupled to the shaft proximally of the first treatment assembly 20. As shown in FIG. 1, the first treatment assembly 20 may be affixed to the distal portion of the shaft 16, and may include a distal tip or dome housing 22 and a first array of electrodes (24a, 24b . . . collectively referred to as '24') for measuring or detecting a monophasic action potential. The electrodes 24 may have a partially spherical recording surface with a relatively small outer diameter, such as outer diameters of about one-half to two millimeters. In one example they may have a diameter of one millimeter. In the arrangement shown in FIG. 1, the electrodes 24 of the first array are each positioned an equal radial distance from a longitudinal axis 30 in different radial directions. While the first array is illustrated as containing four electrodes, one or more electrodes in any suitable configuration may be implemented. The electrodes may be made of one or more non-polarizing materials, such as silver, silver chloride, platinum, iridium, titanium nitride, gold, stainless steel, aluminum, and alloys and combinations thereof for example, to improve the fidelity of MAP electrograms.

The first array of electrodes 24 defines a distal recording geometry, which may have substantially radial symmetry around a longitudinal axis 30 of the shaft 16. For example, an orthogonal array of the four electrodes of the first array 24 is shown, with each electrode positioned at ninety degrees relative to the adjacent electrodes around a circumference of the distal recording geometry. The dome housing 22 may have a series of recesses or sockets 32 for receiving the electrodes in such a fixed spatial arrangement. Specifically in FIG. 1, there are four sockets 32, each partially receiving one of the electrodes 24. In this arrangement, each recording electrode 24 protrudes from the dome housing 22 in the distal direction and a radial direction to enhance the likelihood that at least one electrode of the array will achieve suitable contact with the tissue when the shaft 16 is advanced in the distal direction toward the tissue selected for treatment. This arrangement with biaxial protrusion beyond the dome housing 22 also enhances the depolarizing effect of the first array of electrodes 24.

The dome housing 22 may be made of various materials, including polymers or metals. If the dome housing 22 is made of a polymer, such as polyether-ether-ketone (PEEK), polysulfone, polyurethane, acetal, or other similar engineering plastic, it will have an electrically insulating effect to isolate the first electrode array 24. Alternately, the dome housing 22 may be made of an electrically conductive material, for example selected from the group consisting of silver, silver chloride, platinum, iridium, gold, stainless steel, aluminum, and alloys and combinations thereof. If the dome housing 22 is made of metal, an insulating material such as one or more polymers may be provided between the dome housing 22 and the electrodes 24, and the dome housing 22 may further serve as a conduit for the delivery of radiofrequency ablation energy.

The second treatment assembly 34 may include a second electrode array 26 for measuring or detecting a monophasic action potential. The second array 26 may be constructed of similar materials and have similar features to that of the first array of electrodes 24. The second electrode array 26 may be positioned proximally of the first electrode array 24 and may also be positioned about a discrete portion of the circumference of a lateral portion of the shaft 16 to provide an additional and/or alternative site for monitoring or measuring electrical activity of the tissue, e.g., to obtain a clearer MAP signal with greater fidelity from epicardial tissue. For example, where the surrounding tissue environment impedes adequate positioning of the first electrode array 24 in suitable contact with tissue to obtain a measurement and/or deliver therapeutic energy, the second electrode array 24 may be used to record or otherwise obtain the desired information. In a particular example, the epicardium and the enclosed spaces afforded to medical devices accessing the epicardium are anatomically different than the endocardium. In an epicardial approach, there is often significant contact between portions of a device shaft with the surrounding tissue. The position of the second electrode array 26 on the shaft (as opposed to the distal portion or end location of the first electrode array 24) may be provided to facilitate positive contact with selected epicardial tissue, while the distal end or tip position of the first electrode array 24 may be more suited for recording endocardial activity within one or more chambers of the heart.

The medical device 12 may further include an additional electrode 28 on the shaft 16 for determining a potential with relation to a corresponding potential obtained from the first electrode array 24 and/or the second electrode array 26. The additional electrode 28 may be positioned a pre-determined distance proximal of the first electrode array 24, and another pre-determined distance proximal of the second electrode array 26. A dedicated pacing electrode 38 may also be included for synchronizing the MAP signals from the first and/or second electrode arrays to a local heartbeat. The additional electrode 28 and pacing electrode 38 may have relatively smooth outer surfaces with minimal or no protrusion. The additional electrode 28 and pacing electrode 38 may include substantially cylindrical bands surrounding or otherwise attached to the shaft 16 coaxial with the longitudinal axis as depicted in FIG. 1. These electrodes may be flush with the outer surface of the shaft 16, or may be recessed to reduce a possibility of direct or depolarizing contact with tissue. Alternatively, the additional electrode 28 may be recessed, while the pacing electrode 38 may be larger to increase its exposure and contact with tissue to be paced.

Each electrode of the first and second arrays, as well as the additional electrode 28 and pacing electrode 38 may have a substantially equivalent surface area to optimize the electrical signals obtained from the various electrodes during their operation.

The medical device may also have a mechanism to indicate where at least one component is currently positioned during the phases of a medical treatment. For example, the real-time location of the first electrode array 24 and the second electrode array 26, as well as the additional electrode 28 and the pacing electrode 38 may be indicated with one or more markers such as a radiopaque marker 110.

Figure 2:
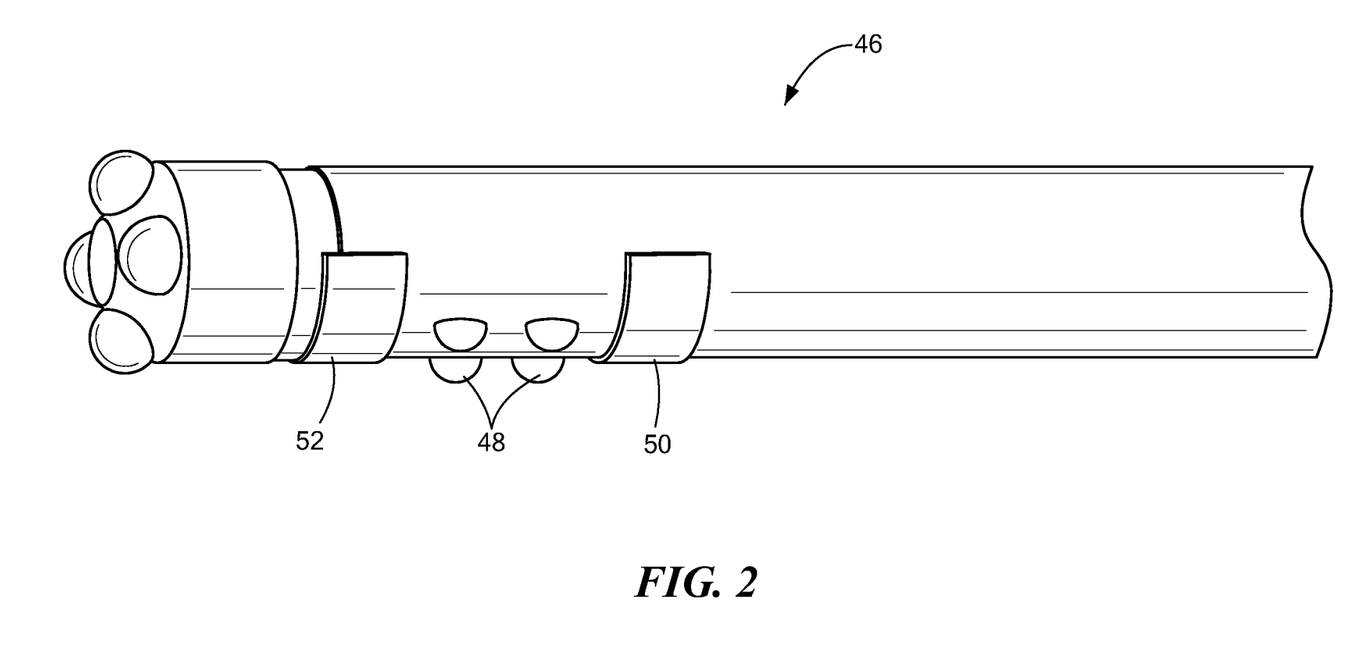
FIG. 2 is an illustration of an exemplary medical device constructed in accordance with the principles of the present invention.

Referring now to FIG. 2, a distal portion of a medical device 46 is shown which includes one or more electrodes for ablation. For example, a second treatment assembly may include four electrodes 48, additional electrodes 50 and 52 which may be used for recording MAP signals, pacing electrical tissue activity, and/or delivering radiofrequency energy to the contacted tissue. For example, after mapping aberrant tissue with the electrodes 48, 50 and/or 52, the electrodes 50, 52 can also serve as radiofrequency ("RF") ablation electrodes in a bipolar or unipolar modality to ablate the selected tissue. Alternatively, electrodes 48 may also serve as RF ablation electrodes. The electrodes 50, 52 may have any suitable shape or configuration. In the example of FIG. 2, they are shown as semi-cylindrical bands, limited to half the circumference of the catheter shaft, so as to focus RF energy more specifically to the tissue selected for treatment.

Figure 3:
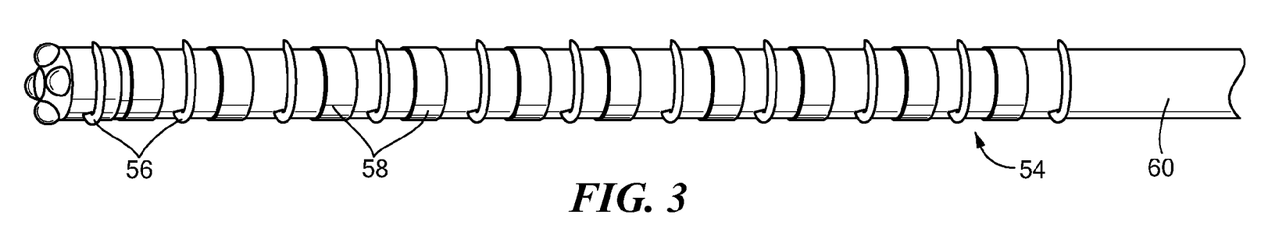
FIG. 3 is an illustration of another exemplary medical device constructed in accordance with the principles of the present invention.

Now referring to FIG. 3, a distal portion of a medical device 54 is shown with a different example of a second treatment assembly, including an alternating series of ring-shaped first electrodes 56 and second electrodes 58 coupled to a sidewall of a shaft 60. The first electrodes 56 protrude from the shaft 60, and have a relatively small longitudinal size or length to aid in temporarily depolarizing tissue. The addition of multiple second electrodes 58 along the shaft 60 allows multiple measurements to be taken along a length of the shaft (and thus the tissue in proximity to the shaft) without having to substantially reposition or move the device.

Figure 3A:
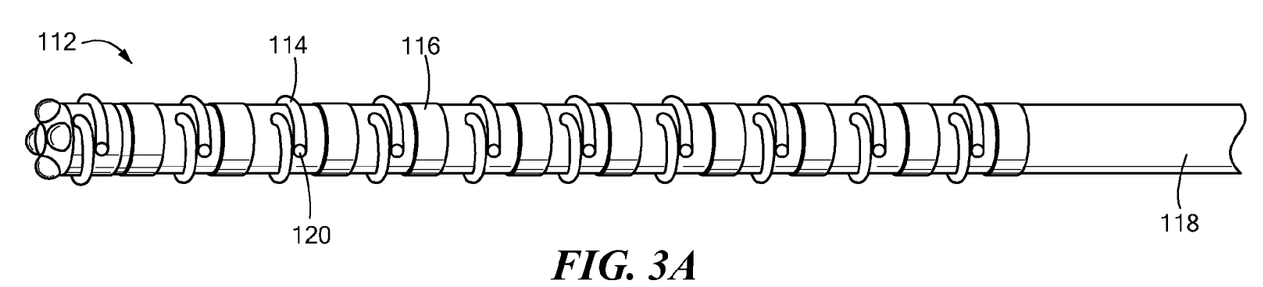
FIGS. 3A-3D are illustrations of additional exemplary medical devices constructed in accordance with the principles of the present invention.

Referring to FIG. 3A, a distal portion of another medical device 112 is shown with an example of a second treatment assembly, having an alternating series of ring-shaped first electrodes 114 and second electrodes 116 coupled to a shaft 118. In the example of FIG. 3A, the first electrodes 114 protrude radially from the shaft 118, and have a relatively small longitudinal size or length to aid in temporarily depolarizing tissue. The first electrodes 114 may have a circumferential or ring shape, with at least a first end affixed to the shaft 118 while the remainder of the first electrodes 114 are wrapped around the shaft 118. Alternatively, different amounts of the first electrodes 114 may be affixed to the shaft 118, such as for example just a first end and a second end, the full length of first electrodes, or one or more portions of first electrodes 114. Some or all of first electrodes 114 are electrically conductive, for example an outer surface, a portion thereof, or the entirety of first electrodes 114. The second electrodes 116 may have a cylindrical shape as shown in FIG. 3A or any other suitable configuration. The addition of multiple second electrodes 116 along the shaft 118 allows multiple measurements to be taken along a length of the shaft (and thus the tissue in proximity to the shaft) without having to substantially reposition or move the device.

To enhance the quality of monophasic action potential signals obtained from the first electrodes 114 and the second electrodes 116, it may be desirable to selectively add a conductive fluid or other signal-enhancing agent in the local region of a treatment assembly. For example, the introduction of saline solution in the vicinity of the first electrodes 114 and the second electrodes 116 may improve the quality (such as amplitude, persistence, and fidelity) of the resulting signals.

Moreover, delivering fluid through the first electrodes 114 during ablation will tend to cool them and lower their operating temperatures.

As shown in FIG. 3A, the first electrodes 114 may have a lumen with a first end connecting to the shaft 118 and a lumen defined thereby, and a second end opening in a delivery port 120. As a specific example, the first electrodes 114 may be formed of metal hypotube material. Accordingly, the physician may selectively administer the signal-enhancing agent such as saline solution through the shaft lumen, through the lumen in the first electrodes 114, out the delivery ports 120. In addition, saline evacuation ports may be incorporated into the shaft to evacuate excess saline from the field of the ablation. This evacuation prevents the saline from conducting ablation energy towards extra-cardiac or other tissues. Evacuation of open flowing saline may also be accomplished through a delivery sheath. Alternatively, the saline may flow through the first electrodes 114 and return through another catheter lumen which carries the fluid back out of the treatment area in a closed-loop manner. Open saline delivery to the pericardial space may be avoided with a closed-loop configuration or a refrigerant-cooled system.

Figure 3B:
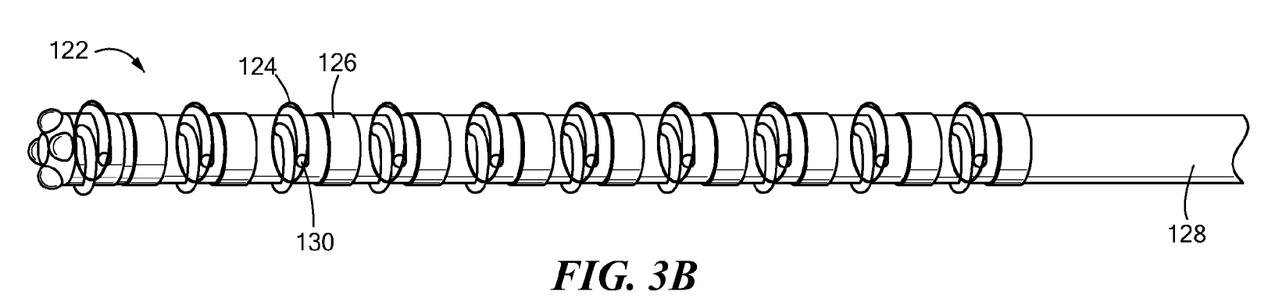

Referring to FIG. 3B, a distal portion of another medical device 122 is shown with another example of a second treatment assembly similar to that shown in FIG. 3A, having an alternating series of ring-shaped first electrodes 124 and second electrodes 126 coupled to a shaft 128. In the example of FIG. 3B, an effective portion of the first electrodes 124 may be directed toward to a specific region of a patient's anatomy, such as for example a selected portion of the surface of the shaft 128. Such an arrangement may enable a physician to limit collection of monophasic action potential signals in a specific direction, and may deliver energy in that specific direction. For example, the desired direction for obtaining signals and/or delivering energy may be toward specific tissue such as the epicardium. This selected effective portion may be limited to a small angular direction, or approximately half of the radial directions or 180 degrees, or a majority of the circumference of the shaft 128. In addition, the effective portions of the first electrodes 124 may all be arranged in the same radial direction, or in different directions such as a staggered arrangement, alternating directions, etc. The effective portions of the first electrodes 124 may be achieved in various ways, including insulating some of each of the first electrodes 124, or for example making the first electrodes 124 of an electrically conductive material for the effective portions and a non-conductive material for other portions of the first electrodes 124. An example of an electrically insulating material may be a polymer layer or coating, insulative potting, an insulating spray, etc. The first electrodes 124 may also have a lumen for providing a conductive or signal-enhancing agent such as saline solution from a series of delivery ports 130.

Figure 3C:
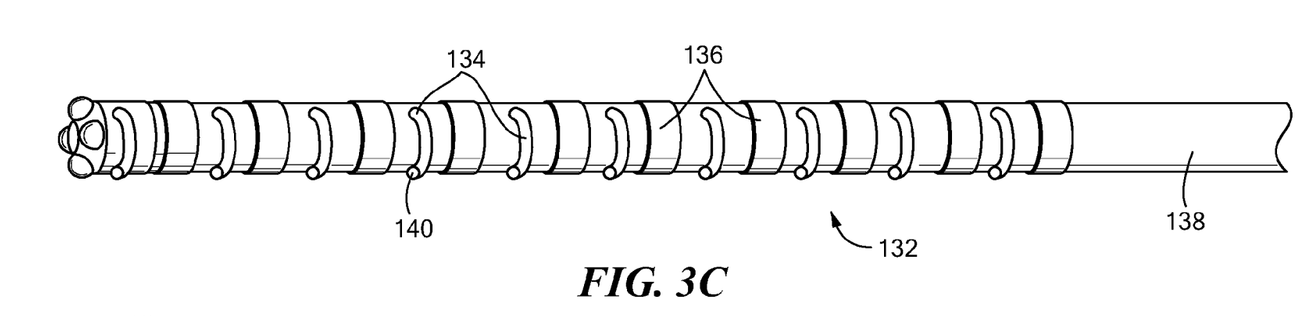
Figure 3D:
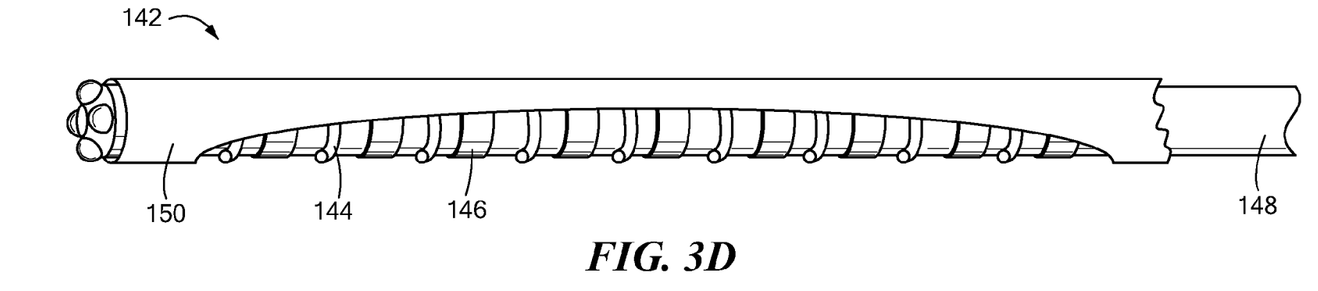

Referring to FIG. 3C, a distal portion of another medical device 132 is shown with another example of a second treatment assembly similar to that shown in FIG. 3B, having an alternating series of first electrodes 134 and second electrodes 136 coupled to a shaft 138. In the example of FIG. 3B, the first electrodes 134 extend around an angular portion of the shaft 138. Such an arrangement may also enable a physician to limit collection of monophasic action potential signals in a specific direction, for example toward to a specific region of a patient's anatomy, and deliver energy in that specific direction. This selected effective portion may be limited to a small angular direction, or approximately half of the radial directions or 180 degrees, or a majority of the circumference of the shaft 128. This arrangement of the first electrodes 134 extending partially around the shaft 138 defines their effective portions without an insulating material as shown in the example of FIG. 3D. The first electrodes 134 may also have a lumen for providing a conductive or signal-enhancing agent such as saline solution from a series of delivery ports 140.

Referring to FIG. 3D, a distal portion of another medical device 142 is shown with another example of a second treatment assembly similar to that shown in FIG. 3C, having an alternating series of first electrodes 144 and second electrodes 146 coupled to a shaft 148, as well as a sheath 150 with a side aperture or window. The sheath may thus cover a portion of the second electrodes 146, with the side window exposing another portion of the second electrodes 146. In the example of FIG. 3D, the sheath 150 enables a physician to collect monophasic action potential signals, and also the deliver ablation energy, in a selected direction or directions. In addition, the sheath 150 can be rotated slightly, for example to selectively treat a larger angular area. Moreover, the sheath 150 can be removed, so as to treat the full extent of the anatomy near the first electrodes 144 and the second electrodes 146. The sheath 150 may also have a steering system, to enable selective deflection of one or more portions of the sheath 150 in various directions, and to advance the medical device 142 or otherwise treat selected anatomy.

Figure 4:
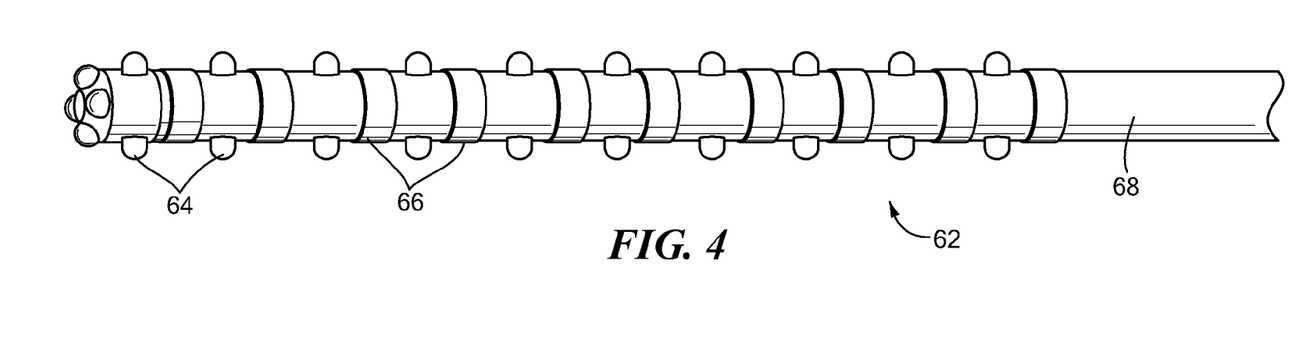
FIG. 4 is an illustration of another exemplary medical device constructed in accordance with the principles of the present invention.

Referring to FIG. 4, a distal portion of another medical device 62 is shown with another example of a second treatment assembly, having an alternating first series of electrodes 64 and a second series of electrodes 66 coupled to a sidewall of a catheter shaft 68. The first electrodes 64 are not ring-shaped as shown in FIG. 3, but rather protrude from the catheter shaft 68 in discrete radial directions approximately 180 degrees apart from one another. The circumferential separation or alignment of the electrodes 64 may coincide with a plane of deflection or steering direction of the shaft. Alternately, a first series of electrodes may protrude from the catheter shaft 68 in different radial directions, for example 60 degrees apart from one another.

Figure 5:
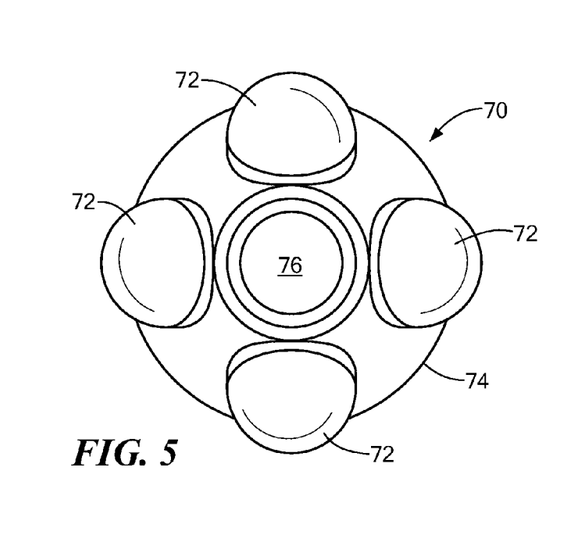
FIG. 5 is an illustration of yet another exemplary medical device constructed in accordance with the principles of the present invention.
Figure 6:
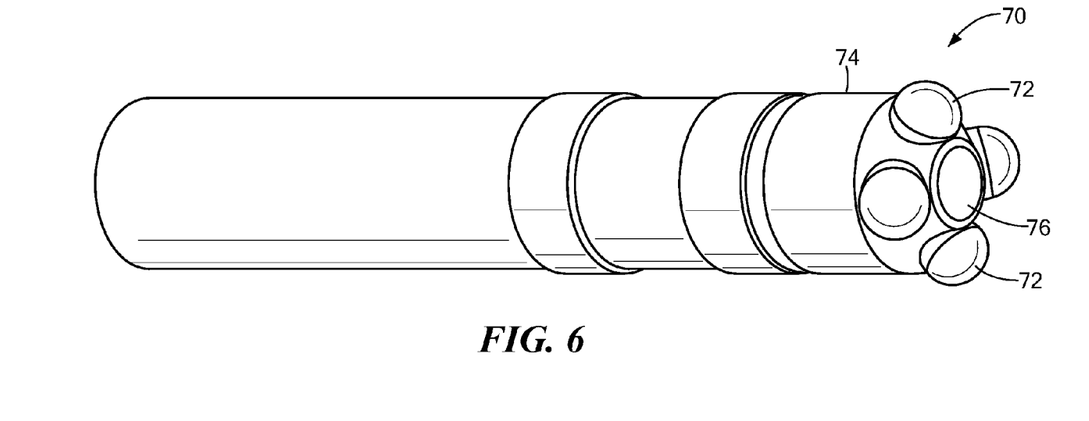
FIG. 6 is a side view of the medical device of FIG. 5.

Referring to FIGS. 5 and 6, a distal portion of another medical device 70 is shown, having four electrodes 72 received within a dome housing 74, and a recessed electrode 76. Recessed electrode 76 is shown in a hemi-spherical recess in the distal surface of the dome housing 74, positioned on the longitudinal axis. This configuration can obtain a MAP signal from one or more of the electrodes 72 with relation to the recessed electrode 76, when the distal tip of the medical device 70 is directly contacting a tissue site, such as within the epicardium of the heart.

Figure 7:
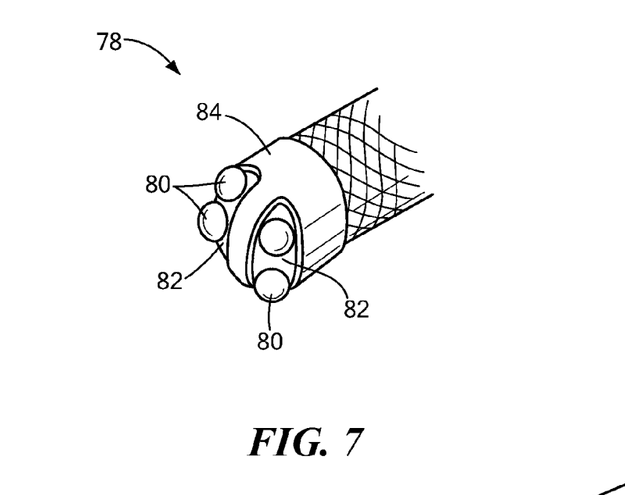
FIG. 7 is an illustration of an exemplary medical device constructed in accordance with the principles of the present invention.
Figure 8:
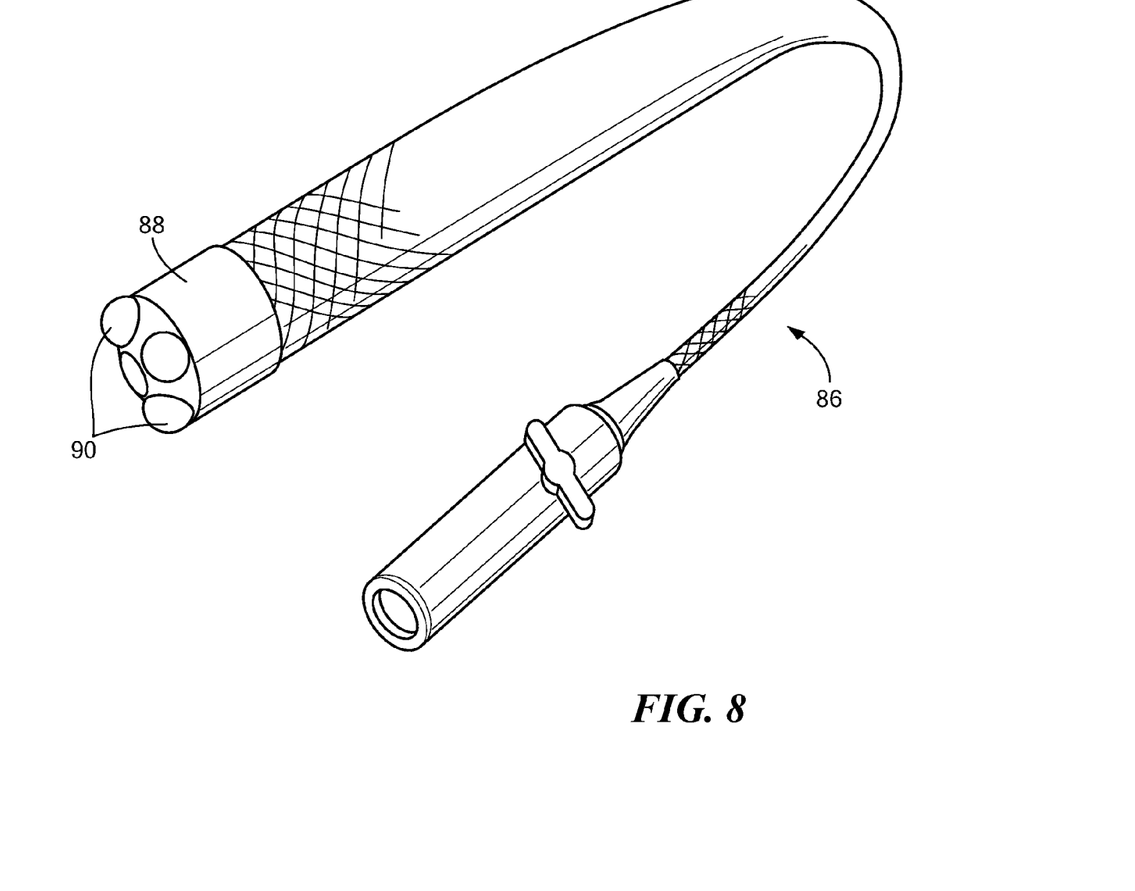
FIG. 8 is an illustration of another exemplary medical device constructed in accordance with the principles of the present invention.

Referring to FIG. 7, a distal portion of another medical device 78 is shown, having four recording electrodes 80 affixed to an insulator 82 on a dome housing 84. The dome housing may be constructed from an electrically conductive material to function as both a reference electrode in recording action potentials in conjunction with the recording electrodes 80 as well as a conduit for radiofrequency ablation energy. Referring to FIG. 8, another medical device 86 is shown, having a unitary distal tip 88 which has four protrusions 90. The single-piece distal tip 88 can be used to monitor, detect or otherwise measure MAP signals, while reducing the number of components and associated complexity with manufacturing and assembly of the device.

Figure 9:
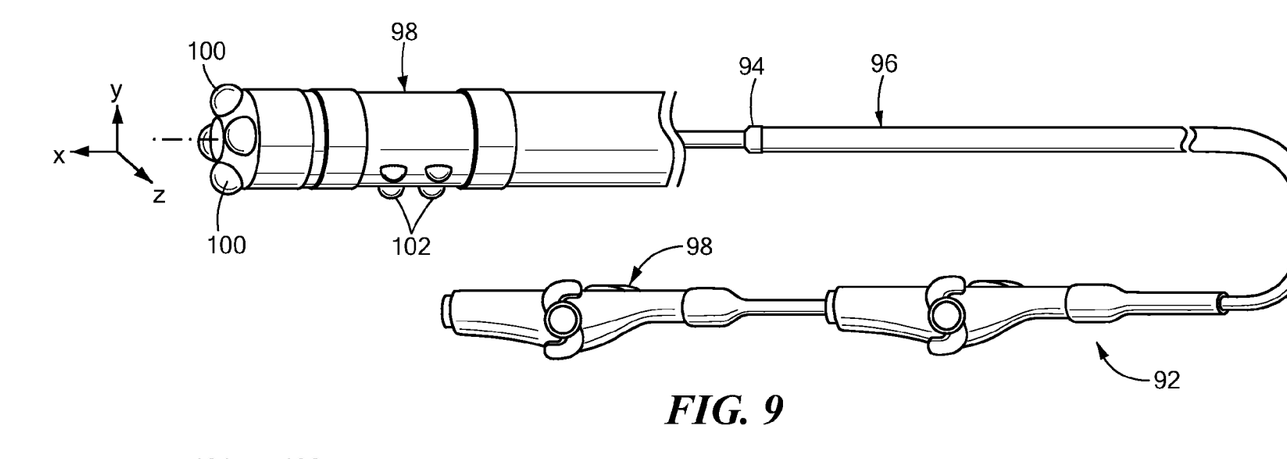
FIG. 9 is an illustration of an exemplary medical system constructed in accordance with the principles of the present invention.

Referring to FIG. 9, a medical system 92 is shown in which an electrode 94 is alternatively positioned on the distal end of an outer sheath 96. A medical catheter 98 is slidably disposed through a lumen defined by the sheath. Medical system 92 allows a physician to customize and adjust the distance between the electrode 94 and the positions of a first treatment array of electrodes 100 and a second treatment array of electrodes 102.

Figure 10:
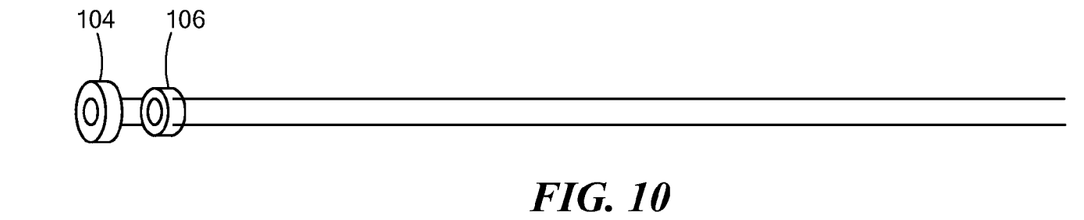
FIG. 10 is an illustration of a medical device constructed in accordance with the principles of the present invention.
Figure 11:
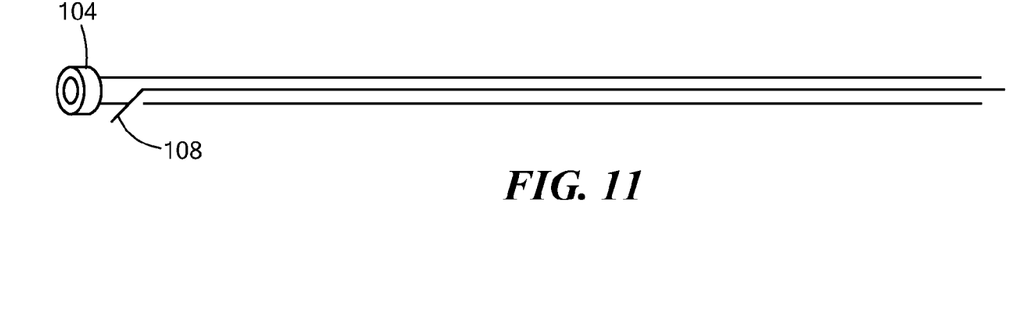
FIG. 11 is an illustration of another exemplary medical device constructed in accordance with the principles of the present invention.

FIG. 10 shows a medical device having a first electrode 104 and a second electrode 106. The first electrode 104 may have larger dimensions than the second electrode 106, allowing it to exert sufficient force against a targeted tissue area to generate a depolarization while the proximal, recording electrode has a decreased contact force with the associated tissue due to its reduced size. FIG. 11 shows a medical device having a first electrode 104 and a second electrode which takes the form of a retractable needle electrode 108. The retractable needle electrode 108 may protrude a short distance from the device shaft sufficient to cause a depolarization of the contacted tissue while also causing very little damage to the tissue.

Figure 12:
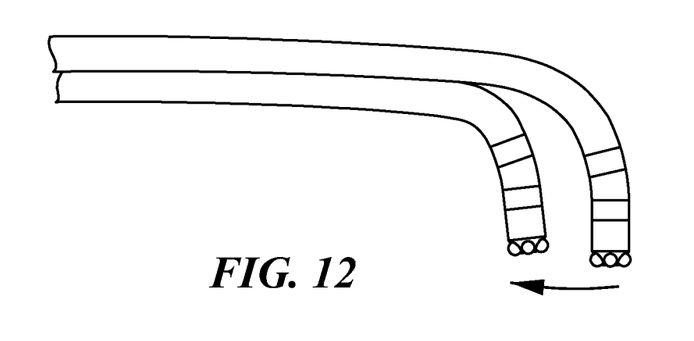
FIG. 12 is an illustration of exemplary deflection profiles of the medical device of FIG. 1.
Figure 13:
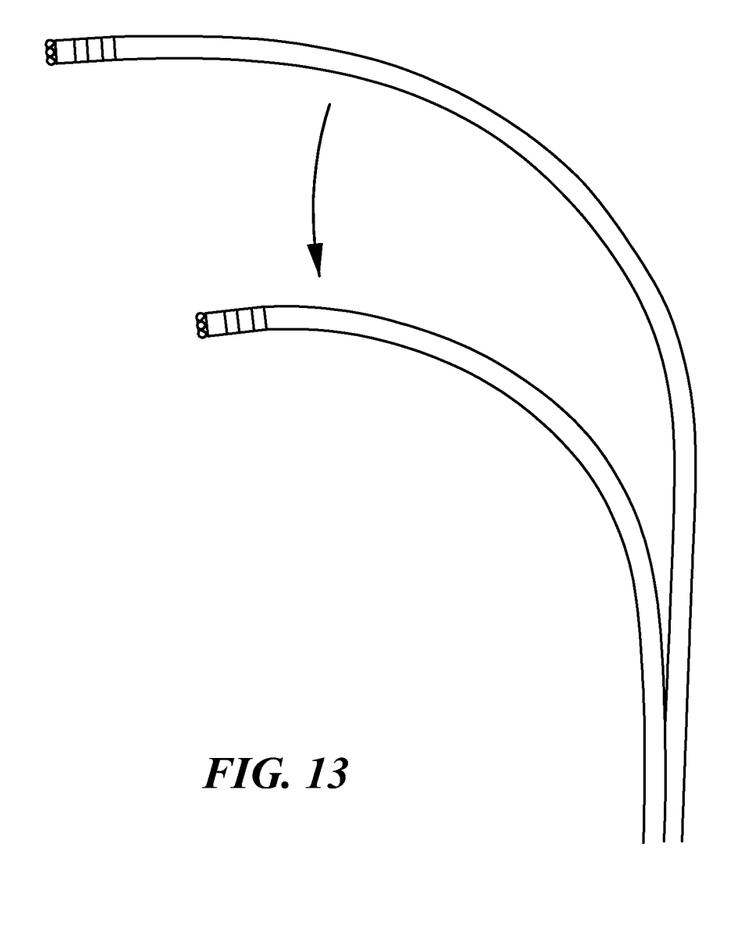
FIG. 13 is an illustration of additional exemplary deflection profiles of the medical device of FIG. 1.

As shown in FIGS. 1, 8, 9 and 14, each of the medical devices disclosed herein may include a handle 18 shaped for ease of use, and may have one or more controls for manipulating one or more portions of the shafts, treatment assemblies, electrode arrays, or the like. Referring to FIG. 1, for example, the handle 18 may have at least one steering control 40, which can be manipulated to cause bending at the line A-A. In particular for access to epicardial tissue, a steering system of the catheter may provide bending either "into the page" or "out of the page" of FIG. 1, which may be described according to the illustrated orthogonal axes as bending of the distal tip along the Z axis. The steering system may provide progressive bending in one or more directions, to enable a physician to steer the catheter system and direct the treatment assemblies toward contact with the desired tissue for treatment. An example of a catheter with a steering system is shown in FIG. 12, which depicts a catheter bending around a distal curve. Also, the steering system may have at least one additional axis or region of bending, for example a proximal curve region as shown in FIG. 13. While the distal treatment assembly is in the enclosed spaces of a minimally-invasive procedure, the practitioner can bend the catheter shaft in this way so it will tend to twist and orient the catheter shaft 16 such that either of the first and second treatment assemblies and their respective electrode arrays will contact the selected tissue.

Specifically, a catheter steering system with a more proximal large curve section as shown in FIG. 13 may be used to steer and direct the catheter within the pericardial space. A catheter steering system with a more distal curve section as shown in FIG. 12 may be deflectable in a direction that is transverse to the plane of the more proximal steering section. This type of compound steering system enables general direction of the catheter with the proximal curve section, while allowing deflection of the tip to deflect in a direction that may be perpendicular to the bending plane of the proximal curve section. The distal steering section may allow for a sharp curve with relatively small bending radius to improve contact with the epicardial surface, enhancing the monophasic action potential signals. In particular, this distal deflection may facilitate guiding the tip through layers of epicardial fat that may be present, make positive contact with the epicardium and obtain monophasic action potential signals.

Additional possible features that may be provided on the handle include an actuation switch or configuration controls, a strain relief, and a coupling for the conduit connecting the catheter handle 18 to the console 14. The console 14 may have suitable components for obtaining signals and potentials from the electrodes, and may also include one or more sensors to monitor the operating parameters throughout the system, including for example, pressure, temperature, flow rates, volume, or similar measurements in the console or the medical device. The console may also have a radio-frequency ("RF") generator 42 to generate RF ablation energy and deliver it to an ablation electrode. The electrical potential measured between the first or second electrode arrays and the additional electrode 28 may be displayed or otherwise presented to the physician on a display 44 for use in treating the patient. These signals may of course be displayed as desired, such as for example individually, in the aggregate as one representation, or one or more of the stronger signals may be presented.

Figure 14:
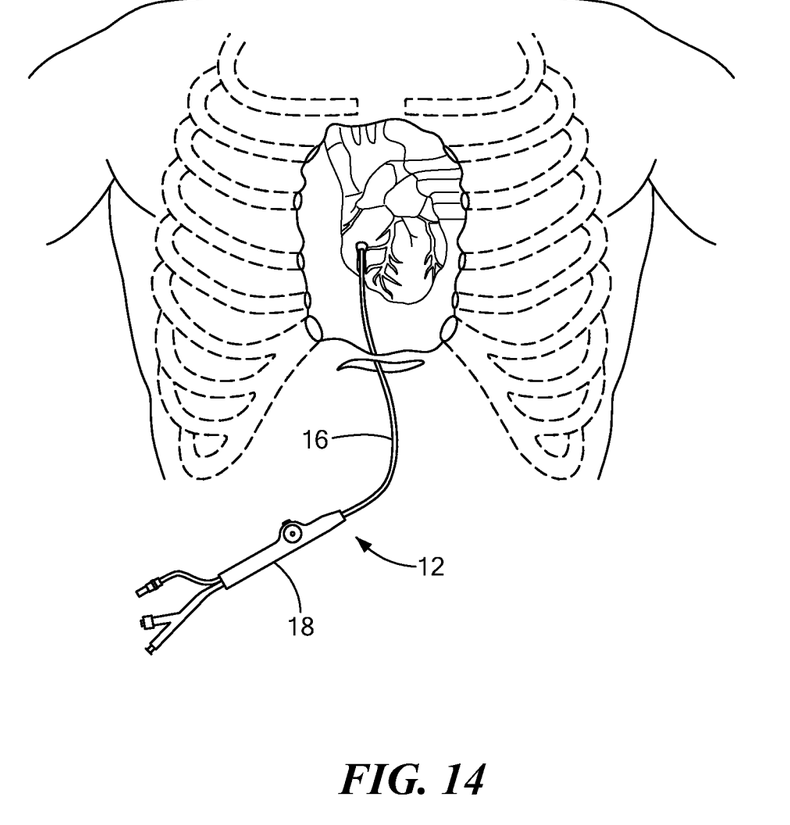
FIG. 14 is an illustration of an exemplary use of the medical device of FIG. 1.

Now referring to FIG. 14, an exemplary use of the medical system 10 is shown. In particular, the distal portion of the medical device 12 may be positioned in proximity to or otherwise adjacent to a target tissue region to be treated. The introduction and positioning of the medical device 12 within the patient may include a percutaneous approach from a subxyphoid incision or one or more small thoracotomy incisions to the epicardial surface of the heart, as shown in FIG. 12. Another access method may use a needle advanced to the pericardium, guiding advancement of a dilator and sheath into the pericardial space, which provides for a smaller incision. The introduction and positioning of access tools can be guided by use of visualization, imaging and dissection techniques, including, for example, fluoroscopy imaging in an intravascular procedure and/or video thoracoscope in a minimally invasive surgical procedure.

Once the medical device 12 has been positioned in the vicinity of the tissue to be treated, the first or second electrode array may be placed in contact with the selected tissue region, which may include cardiac tissue, for example. For example, the first electrode array 24 may be easier to navigate and deflect into appropriate contact with a targeted tissue site within the relatively expansive interior chambers of the heart. Alternatively, the second electrode array 26 may be more suitable for contacting a comparatively restrictive epicardial surface of the heart for diagnosis and treatment. The positioning of the medical device 12 may include steering or deflecting at least a distal portion of the catheter shaft 16. The medical device can be manipulated to apply local pressure from at least one electrode of the respective arrays to the tissue, causing local depolarization to obtain at least one monophasic action potential signal. In particular, steering control 40 may be actuated to cause bending of the catheter shaft 16 in a selected direction at one or more positions. For example, steering control may cause bending of the catheter shaft 16 at line A-A along the Z axis, to orient either the distally-oriented first electrode array 24 or the laterally-oriented second electrode array 26 to contact the desired tissue.

The steering control may also enable bending of the catheter shaft 16 in a distal curve and a proximal curve, as shown in FIGS. 12 and 13 respectively. The features of the medical systems and devices according to the present invention provide multiple electrode arrays to facilitate enhanced contact with restrictive tissue areas with a single device to thus improve signal fidelity and treatment efficacy. When an acceptable MAP signal is obtained from at least one recording electrode or counter electrode with reference to a reference electrode, the physician can diagnose and treat the patient accordingly. Such treatment may involve delivering RF energy from a generator to an ablation electrode.

Figure 15A:
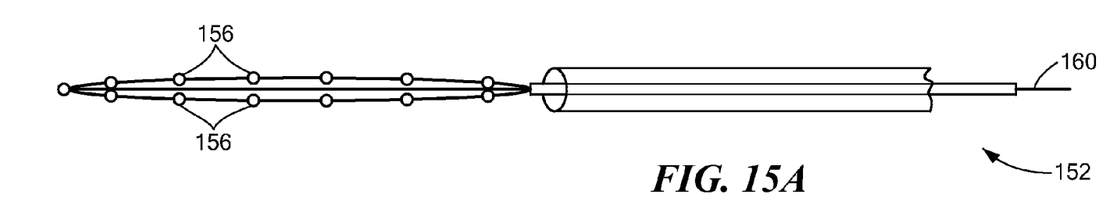
FIGS. 15A-15C are illustrations of additional exemplary medical devices constructed in accordance with the principles of the present invention.
Figure 15B:
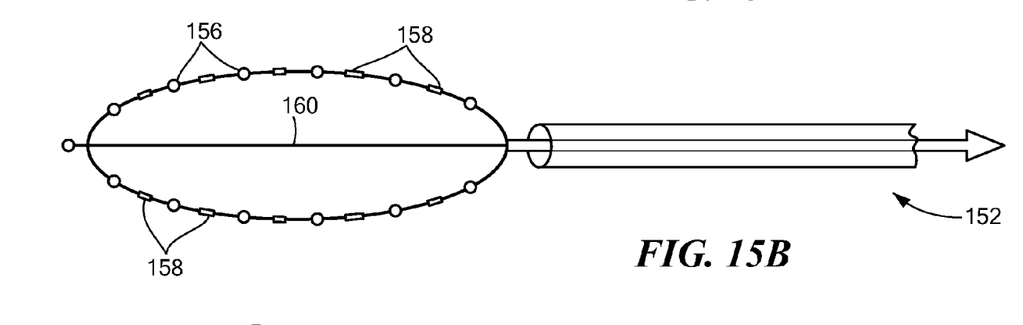
Figure 15C:
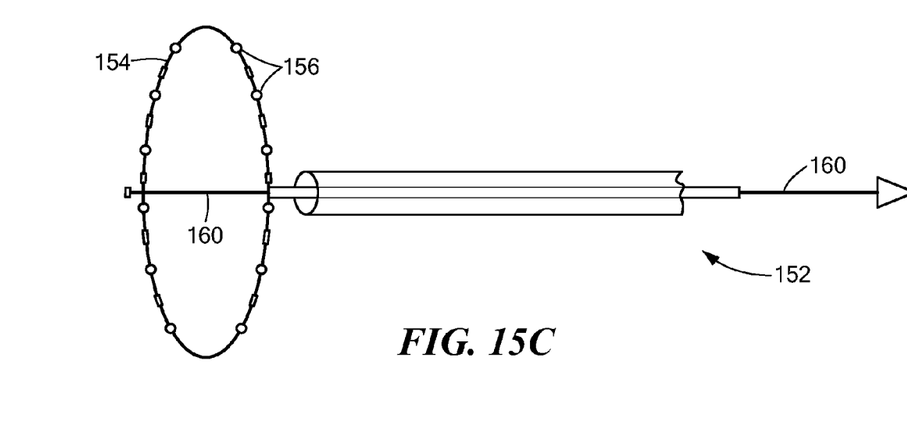

Now referring to FIGS. 15A-C, a distal portion of a medical device 152 is shown with a different example of a treatment assembly, including a loop or ring 154 with an alternating series of first electrodes 156 and second electrodes 158. The first electrodes 156 protrude from the resilient ring 154, and may have a relatively small rounded size aid in temporarily depolarizing tissue. The second electrodes 158 are also affixed to the ring 154 and may be interspersed among the first electrodes 156 to obtain monophasic action potential signals, allowing multiple measurements to be taken along the path of the ring 154 without having to substantially reposition or move the device. Of course, the treatment assembly may have any suitable shape, including circular, oval, polygonal, or irregular. The shape of the treatment assembly may also be selected to correspond with specific anatomy.

The treatment assembly may be made of any suitable materials having the desired characteristics, for example biocompatible, shapeable, elastic, or resilient. The shape of the treatment assembly may be adjusted during treatment with various shaping elements, which enables transformation of the treatment assembly from a deployment shape such as shown in FIG. 15A to a variety of treatment shapes as shown for example in FIG. 15B and FIG. 15C. Accordingly, an adjustable treatment array enables mapping and ablation of a customizable treatment area of various shapes and sizes, depending on how much the array is expanded or manipulated. Also, the treatment array may be pre-shaped in many configurations and sizes for specific targeted anatomical sites. An example shaping element is illustrated as an actuator 160 affixed to the ring 154. The actuator 160 can be extended or retracted to configure the treatment assembly and contract or expand the ring 154.

In another example, the medical device may have electrodes arranged only on one side of the treatment array, to more specifically contact, map and treat selected tissues, such as for example the epicardial surface of the heart. During ablation, it may be desirable to cool the electrodes using for example closed loop or open loop flow of saline or internal refrigerant.

It will be appreciated by persons skilled in the art that the present invention is not limited to what has been particularly shown and described herein above. Of note, while certain components, such as the various electrodes or other items disclosed herein, are indicated as mapping, reference, and/or recording electrodes, it is understood these are exemplary functions that do not limit additional uses of the designated electrodes or components for alternative functions. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   a shaft having a distal portion;
   a first electrode array coupled to the distal portion;
   a second electrode array including at least two ring-shaped electrodes coupled to a lateral surface of the shaft proximal to the first array, each ring-shaped electrode of the second electrode array defining an electrically transmissive region and an electrically non-transmissive region, the electrically transmissive regions of the at least two ring-shaped electrodes being oriented in the same radial direction; and
   a third electrode array including at least two ring-shaped electrodes coupled to the shaft proximal to the first array, the electrodes of the third electrode array alternating with the electrodes of the second array.

2. The medical device according to claim 1, wherein the first electrode array includes a plurality of electrodes made of substantially non-polarizable material.

3. The medical device according to claim 1, wherein the first electrode array includes four electrodes equally spaced from a longitudinal axis defined by the shaft.

4. The medical device according to claim 1, wherein the at least two ring-shaped electrodes of the second electrode array protrude a distance away from an outer diameter of the shaft.

5. A medical device, comprising:
   a catheter having a shaft with a distal portion;
   a first plurality of substantially hemispherical electrodes coupled to the distal portion;
   a second plurality of substantially ring-shaped electrodes coupled to and protruding from the shaft proximal of the first plurality of substantially hemispherical electrodes, each substantially ring-shaped electrode of the second plurality of substantially ring-shaped electrodes defining an electrically transmissive region and an electrically non-transmissive region, the electrically transmissive regions of the second plurality of substantially ring-shaped electrodes being oriented in the same radial direction;
   a third plurality of substantially ring-shaped electrodes coupled to the shaft proximal of the first plurality of substantially hemispherical electrodes, each of the electrodes of the second plurality of substantially ring-shaped electrodes being in an alternating position with each of the electrodes of the third plurality of at least substantially ring-shaped electrodes.

6. The medical device according to claim 5, further comprising a console having a processor in electrical communication with the first plurality of substantially hemispherical electrodes, the second plurality of substantially ring-shaped electrodes, and the third plurality of substantially ring-shaped electrodes, the processor programmed to obtain a monophasic action potential recording from at least one of the first plurality of substantially hemispherical electrodes and second plurality of substantially ring-shaped electrodes.

* * * * *